(12) United States Patent
Calder

(10) Patent No.: US 12,133,788 B2
(45) Date of Patent: Nov. 5, 2024

(54) APPLICATORS

(71) Applicant: Simcro Limited

(72) Inventor: David Bain Calder, Ohaupo (NZ)

(73) Assignee: Datamars SA, Lamone (CH)

( * ) Notice: Subject to any disclaimer, the term of this patent is extended or adjusted under 35 U.S.C. 154(b) by 929 days.

(21) Appl. No.: 16/972,585

(22) PCT Filed: Jun. 7, 2019

(86) PCT No.: PCT/NZ2019/050067
§ 371 (c)(1),
(2) Date: Dec. 5, 2020

(87) PCT Pub. No.: WO2019/235943
PCT Pub. Date: Dec. 12, 2019

(65) Prior Publication Data
US 2021/0236254 A1    Aug. 5, 2021

Related U.S. Application Data

(60) Provisional application No. 62/681,669, filed on Jun. 7, 2018.

(51) Int. Cl.
*A61D 7/00* (2006.01)
*A61M 5/31* (2006.01)
*A61M 5/315* (2006.01)

(52) U.S. Cl.
CPC .......... *A61D 7/00* (2013.01); *A61M 5/31563* (2013.01); *A61M 5/31585* (2013.01); *A61M 2005/3128* (2013.01); *A61M 2250/00* (2013.01)

(58) Field of Classification Search
CPC ..... A61D 7/00; A61M 5/204; A61M 5/31511; A61M 5/3137; A61M 5/31581
See application file for complete search history.

(56) References Cited

U.S. PATENT DOCUMENTS 5,037,399 A    6/1991    Reichart et al.
7,357,781 B2 *   4/2008    Menassa ................. A61M 5/30
                                                             604/70

(Continued)

FOREIGN PATENT DOCUMENTS

NZ            228209 A    3/1991
WO    WO2001017436 A1    3/2001

(Continued)

Primary Examiner — Scott J Medway
(74) Attorney, Agent, or Firm — Lowe Graham Jones PLLC

(57) ABSTRACT

Disclosed is an applicator comprising or including, a dosing body including, at least one barrel; a piston moveable within the at least one barrel to stroke between a variable first position and a second position. In use, movement of the piston towards the first position can draw a first fluid into the barrel, and movement of the piston towards the second position can force the first fluid out of the barrel. There is at least one fluid inlet valve to allow the fluid to flow into the at least one barrel at least under action of the piston, and at least one fluid outlet valve to allow the first fluid to flow out of the at least one barrel at least under action of the piston. A piston actuating assembly, selectively engageable with the dosing body, is present, the piston actuator assembly having a user operable handle to drive a second actuation member which in turn can drive the piston between the first position and the second position, the connection between the second actuation member, or part thereof being a releasable one.

14 Claims, 10 Drawing Sheets

(56) References Cited

U.S. PATENT DOCUMENTS

| | | | |
|---|---|---|---|
| 7,988,677 B2* | 8/2011 | Fojtik | A61M 5/31581 |
| | | | 222/472 |
| 8,945,070 B2 | 2/2015 | Holmes et al. | |
| 2010/0076370 A1* | 3/2010 | Howlett | A61M 5/31505 |
| | | | 604/65 |
| 2010/0199984 A1* | 8/2010 | Williams, III | B05B 11/0032 |
| | | | 128/200.23 |
| 2016/0022916 A1* | 1/2016 | Tran | A61M 5/31511 |
| | | | 604/229 |
| 2017/0281875 A1* | 10/2017 | Piehl | A61M 5/002 |
| 2017/0296753 A1 | 10/2017 | Rowe et al. | |
| 2017/0340424 A1 | 11/2017 | Edwards | |
| 2019/0022315 A1* | 1/2019 | Udy | A61M 5/31578 |

FOREIGN PATENT DOCUMENTS

| | | |
|---|---|---|
| WO | WO2011082685 A1 | 7/2011 |
| WO | WO2016138018 A1 | 9/2016 |

* cited by examiner

APPLICATORS

TECHNICAL FIELD OF THE INVENTION

The present invention relates to applicators for fluids and the like.

In particular, though not solely, the present invention is directed to applicators for animals to apply a fluid orally, nasally, topically or subcutaneously to the animal.

BACKGROUND OF THE INVENTION

Animal remedies for sheep, cattle, goats, llama and the like farmed animals for veterinary and/or animal husbandry are applied by a number of methods including topical or "pour-on" application, oral application, injection, including subcutaneous, and nasal infusion. Each of these is typically dispensed from a "pistol grip" style dispenser or applicator.

Typically such applicators have a piston or plunger which can be reciprocated within a barrel by squeezing and releasing a first handle relative to a second handle. The liquid to be dispensed is drawn into the barrel through an inlet via a one-way inlet valve when the plunger is withdrawn inside the barrel, and is dispensed through a nozzle via an outlet valve when the plunger is extended towards the outlet valve. The inlet, barrel, piston and outlet are typically inline. The movement of the handles moves the piston along this line.

As is described above, conventional fluid applicators incorporate two one-way valves. These valves are referred to as the inlet valve and the outlet valve.

The valves are typically biased with springs, so that they open only when there is a predefined difference in the fluid pressure between the upstream side of the valve and the downstream side. Fluid cannot flow backwards through either valve, as flow in this direction will tend to push the valves more tightly closed.

When the applicator is at rest, both valves are closed. When the applicator is in use, it is intended that only one valve opens at a time. During the discharge stroke, the outlet valve is pushed open by the raised fluid pressure within the barrel. During the refill stroke, the inlet valve is pushed open by fluid entering the barrel (where there is now a partial vacuum).

Such an applicator is described in the applicant's New Zealand patent NZ 521084, the contents of which are herein incorporated by reference. The applicator in NZ 521084 typifies the pistol grip form applicator and is one of the most common shapes and lay outs for such applicators.

One shortcoming of the current shape applicators in the in-line nature of the components. The applicator has an inlet, inlet valving, barrel with piston, outlet valving, and applicator, typically all in line above the actuating handles. This makes the applicator quite long. In modern farming practices it is important that the applicator be as compact as possible so as to be easy to use and maneuver in tight environments such as through gaps in a stock chute, or when moving through a herd of animals. Long, potentially delicate applicators of the prior art can get hung up on fences, chutes, animals and the like, and may require more than one hand to locate and operate. This can cause fatigue for the user, and lengthen the time for each applied dose.

A further requirement is to reduce the fatigue of the user, when actuating the applicator to deliver the dose, especially when treating a large number of animals. The dose of most actuators can be adjusted. One way this adjustment is typically done is to limit the start or stop position of the piston's movement in the barrel, that is, its withdrawn position, or its extended position respectively. This method is useful because it is simple and straight forward to implement and is reliable. NZ521084 describes a mechanism comprising a cylindrical dosage control part which is provided with a plurality of stopping ribs, each of a different length. Rotation of the dosage control part allows selection of which of the stopping ribs is engaged by a rib provided on the plunger, and therefor allows adjustment of the maximum stroke of the plunger.

Notably, the dosage control part encircles the plunger, and so the plunger must be of adequate length to allow the plunger to achieve its full or stroke (dependent on the setting of the dosage control part) before the mechanism which actuates the plunger comes into contact with the dosage control part.

In this way the one applicator can be used for a variety of doses, for example depending on animal weight at the time, or overtime.

However, the moving handle is directly connected to the piston. Therefore, whichever position of the piston that is limited results in a shortened stroke of the two handles relative to each other. For example, when a minimal dose is supplied from the applicator the handle stroke is very small. This results in a very small movement of the hand for the user. In contrast the largest dose the applicator can deliver will result in full movement of the two handles relative to each other. Whichever position the handle is in, short stroke for a small dose, or long stroke for maximum dose the user must still overcome the stiction of the piston in the barrel, and the opening pressure required to actuate the valves, for example the outlet valve to deliver the dose, or vice versa. The best leverage for the user to easily exert this required force on the handles is at or near the full movement of the handles. Therefore, a user's hand leverage is compromised when the handles are nearly closed for the smallest dose delivery, yet the user must still overcome this starting force to deliver the dose. This can lead to increased time to dose, fatigue over the short to medium term, and repetitive injury over the long term.

When the applicator is used in the veterinary and/or animal husbandry fields it should preferably have the following characteristics:
  be simple and reliable, suited to use in an agricultural environment.
  be inexpensive to implement.
  not interfere with the dose accuracy of the applicator.
  work regardless of the height of the fluid source relative to the applicator.
  work regardless of the viscosity of the fluid.
  work regardless of the speed of discharge or refill.
  work correctly during all stages of the applicator's operating cycle, including discharge, refill, and unexpected pauses in mid-stroke.
  withstand attack by aggressive chemicals.

Applicators may also require periodic servicing of various inlet and outlet valves in order to stay in good working condition. It is desirable for this servicing to be achievable as quickly and simply as possible. However, many applicators of the prior art have inlet and outlet valves located at a plurality of locations, or require disassembly of parts that do not need servicing to access the areas that need service. Therefore, they require significant disassembly of the applicator for the valves and the like to be serviced.

Another shortcoming of existing applicators is repair. Should apart break on existing applicators then typically the entire applicator must then be thrown away, or recycled, but it cannot be repaired. Existing ones that can be repaired are typically expensively made, or made from expensive materials, and so are less efficient economically.

Modularity is also desirable. Existing applicators are typically manufactured as an all in one. That is, parts from one applicator are not easily used by the end user on another applicator, even from the same manufacturer, save for perhaps the effector that applies the fluid on the animal. Therefore, the one applicator often cannot be used for a range of application tasks, e.g. subcutaneous, topical and oral, because as well as the differing end effector for fluid delivery, the dose of fluid delivered will also vary, from milliliters, or part thereof, to tens of milliliters.

Modularity also brings an advantage to manufacture. In existing integrated units with no interchange of parts between applicator models, then applicators then to manufacture a single unit, requires all parts for that particular unit to be made and assembled. This does not give the manufacturer flexibility.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

It is an object of the present invention to provide an improved applicator, or to overcome the problem of handle movement changing with the dose selected, or to overcome the above shortcomings or address the above *desiderata*, or to at least provide the public with a useful choice.

BRIEF DESCRIPTION OF THE INVENTION

In a first aspect the present invention consists in an applicator comprising or including, A dosing body comprising or including,
at least one barrel;
a piston moveable within the at least one barrel to stroke between a variable first position and a second position, wherein, in use, movement of the piston towards the first position can draw a first fluid into the barrel, and movement of the piston towards the second position can force the first fluid out of the barrel;
at least one fluid inlet valve to allow the fluid to flow into the at least one barrel at least under action of the piston, and at least one fluid outlet valve to allow the first fluid to flow out of the at least one barrel at least under action of the piston;
a piston actuating assembly, selectively engagable with the dosing body, the piston actuator assembly having a user operable handle to drive a second actuation member which in turn can drive the piston between the first position and the second position, the connection between the second actuation member, or part thereof being a releasable one.

Preferably the releasable connection is a magnetic one that attracts and holds the second actuating member to the piston, or part thereof.

Preferably there is a piston shaft between the piston and the second actuating member.

Preferably the piston and barrel are not in line with the piston actuating assembly second actuating means, but rather are at an angle to them, or a main axis of the applicator.

Preferably the stroke of the piston is at or near vertical when the applicator is held normally.

Preferably a handle component extends from the body and the user operated handle pivots from a first pivot point at a distal end of the handle component.

Preferably the user operated handle is driven to extend away from the handle component by a second biasing component.

Preferably the first trigger component is biased to hold the second actuating component in place until that biasing force is overcome by the force of the first biasing component, or by the second trigger component.

Preferably the barrel is replaceable to vary the dose of the applicator.

Alternatively the barrel can receive an insert to provide a stop of the second position of the piston to vary the dose of the applicator.

Alternatively the barrel has a variable stop to vary the second position of the piston to vary the dose of the applicator.

Preferably the inlet valve, applicator, outlet valve, piston and barrel can be removed as an dose assembly from the body.

Preferably the dose assembly engages to the piston actuation assembly via complimentary rails, either side of the dose assembly, between the dose assembly and the piston actuation assembly.

Preferably there is a second actuating component held in position against the force of the first biasing component, a first trigger component that holds the second actuating component in place until a required force is reached by the first biasing component, or a second trigger component releases the first trigger component, whereby the second actuating component is then released and driven by the force of the first biasing component to in turn drive the piston toward the second position.

In another aspect the present invention consists in a method of dispensing a fluid for animal welfare, comprising or including the steps of, A user driving a user operated handle which in turn drives a second actuating component,
Driving a piston via the second actuating component, where the second actuating component is housed in a unitary dose assembly including fluid inlet, inlet valve, barrel, outlet valve and fluid outlet,
Wherein the unitary dose assembly is selectively engageable to a body contained the user operated handle,
Operation of the piston from a first position to a second position driving a dose of fluid from the barrel to the fluid outlet for delivery.

In another aspect the present invention consists in a kit of parts for a applicator including a handle body and a dose assembly as herein described with reference to any one or more of the accompanying drawings.

In another aspect the present invention consists in an applicator as described herein with reference to any one or more of the accompanying drawings.

Throughout the description and the claims, all reference to pressures are to gauge 35 pressures, i.e. pressure relative to the ambient pressure. Therefore, a reference to zero pressure means ambient pressure. Reference to negative pressure means suction.

Reference to a partial vacuum is any pressure below ambient pressure but greater than a total vacuum.

Reference to the "upstream" direction is towards the direction in the fluid flow path from which fluid enters the applicator. Reference to the "downstream" direction is to the direction in which the fluid normally flows.

As used herein the term "and/or" means "and" or "or", or both.

As used herein "(s)" following a noun means the plural and/or singular forms of the noun.

The term "comprising" as used in this specification means "consisting at least in part of". When interpreting statements in this specification which include that term, the features, prefaced by that term in each statement, all need to be present, but other features can also be present. Related terms such as "comprise" and "comprised" are to be interpreted in the same manner.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7).

The entire disclosures of all applications, patents and publications, cited above and below, if any, are hereby incorporated by reference.

This invention may also be said broadly to consist in the parts, elements and features referred to or indicated in the specification of the application, individually or collectively, and any or all combinations of any two or more of said parts, elements and features, and where specific integers are mentioned herein which have known equivalents in the art to which this invention relates, such known equivalents are deemed to be incorporated herein as if individually set forth.

Other aspects of the invention may become apparent from the following description which is given by way of example only and with reference to the accompanying drawings.

BRIEF DESCRIPTION OF THE DRAWINGS

Preferred forms of the present invention will now be described with reference to the accompanying drawings in which.

DETAILED DESCRIPTION OF THE INVENTION

Figure 1:
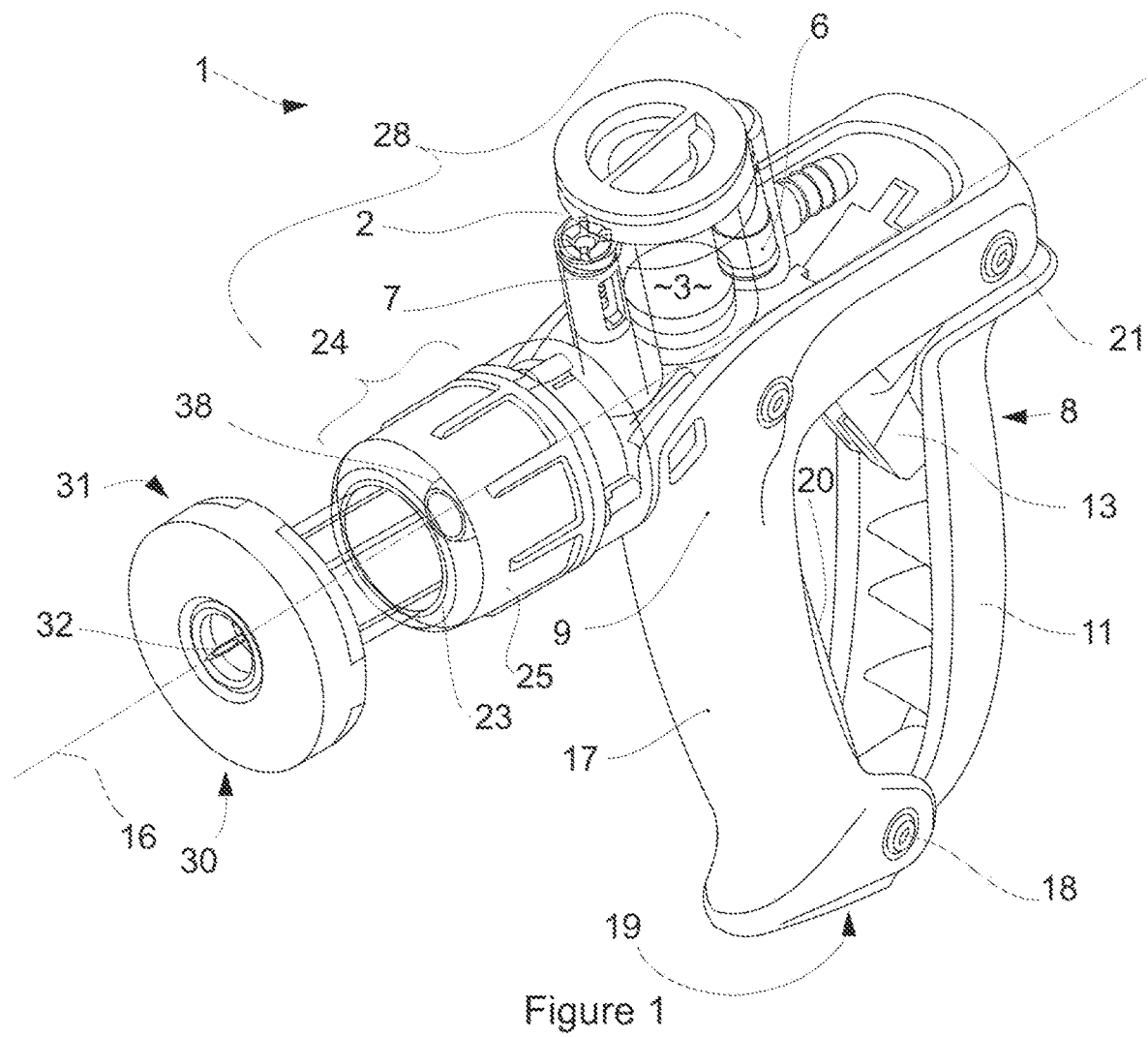
FIG. 1 Shows an isometric view of one form of the applicator showing the barrel and piston out of line with the main axis of the applicator, in this case the applicator is configured with a marking pad, needle and needle guard for marking and applying a subcutaneous injection, FIG. 2 Shows a side view of the embodiment of FIG. 1,
FIG. 3 Shows a plan view of the embodiment of FIG. 1,
FIG. 4 Shows a front view of the embodiment of FIG. 1,
FIG. 5 Shows a rear view of the embodiment of FIG. 1,
FIG. 6 Shows a bottom view of the embodiment of FIG. 1,
FIG. 7 Shows an exploded isometric view of the body and associated components of the embodiment of FIG. 1,
FIG. 8 Shows removed locking barrel and applicator end,
FIG. 9 Shows the Slide out dosing assembly,
FIG. 10 Shows another view of the slide out dosing assembly,
FIG. 11 A close up of the slide out dosing assembly showing the magnetic connection between the piston shaft and actuator, and the complimentary rails between the dosing body and handle assembly,
FIG. 12 Shows a further embodiment of the present applicator, having a differing form of effector, the detent of the dose assembly and handle portion being in a different location,
FIG. 13 Shows a similar close up to that of FIG. 12 of the slide out dosing assembly showing the engaged separable connection between the piston shaft and piston actuator, in this case the connection is a bayonet where a bulge of the piston shaft is captured within a receiving aperture of the piston actuator, and FIG. 14 Shows a similar view to that of FIG. 13, from the side, showing the separable connection disengaged, for example when the dose assembly is being removed, or installed into the handle body.
Figure 2:
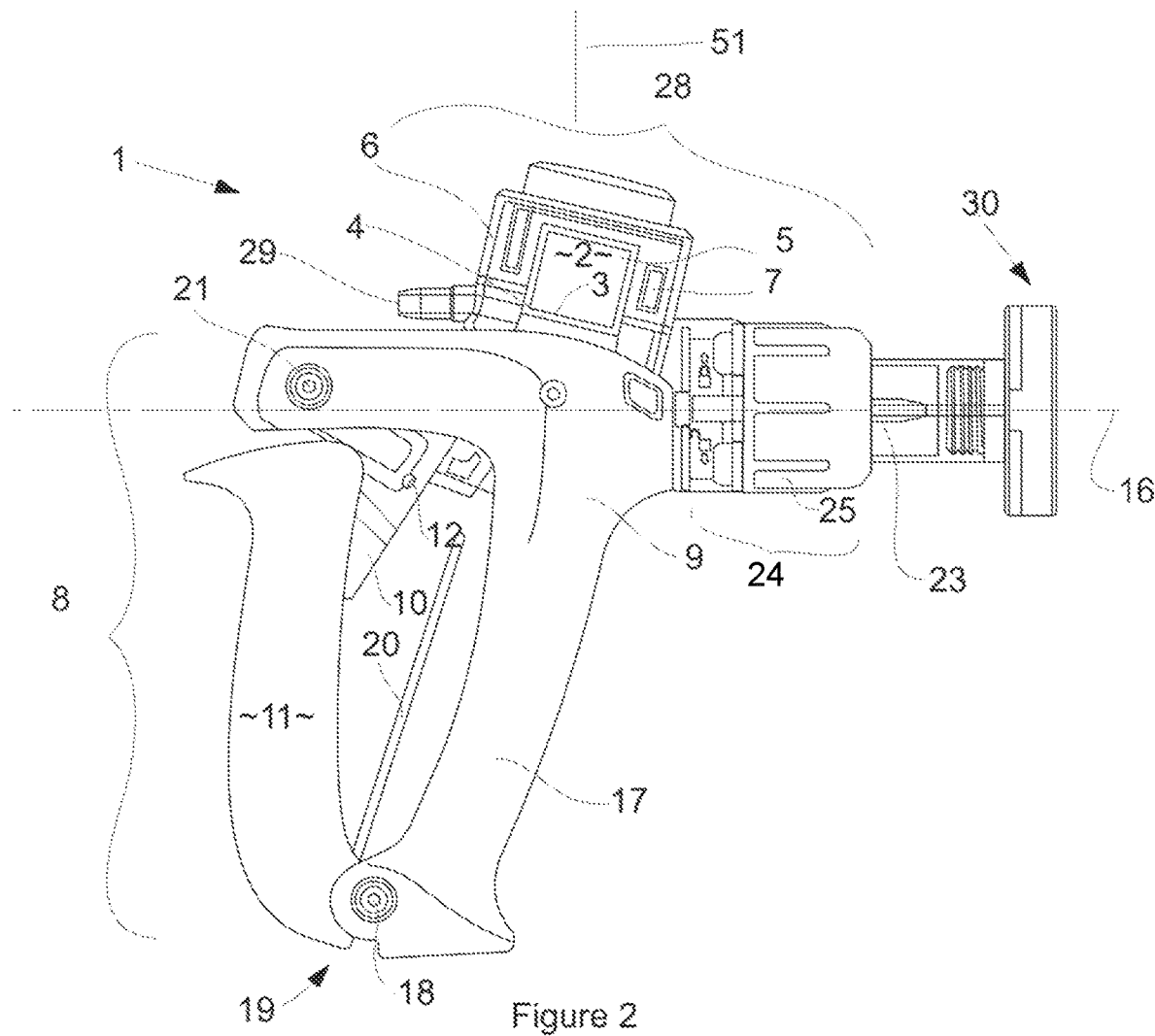
Figure 3:
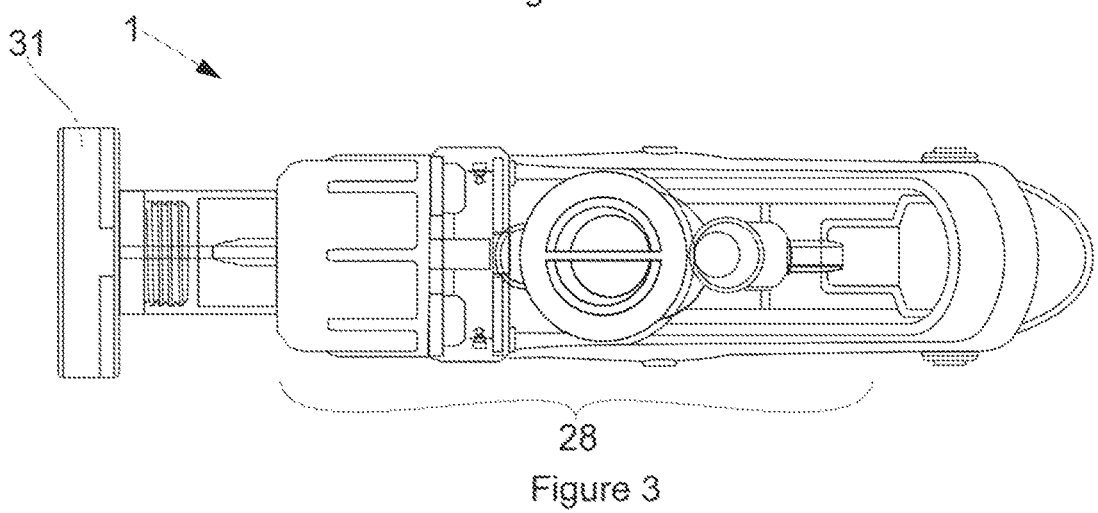
Figure 4:
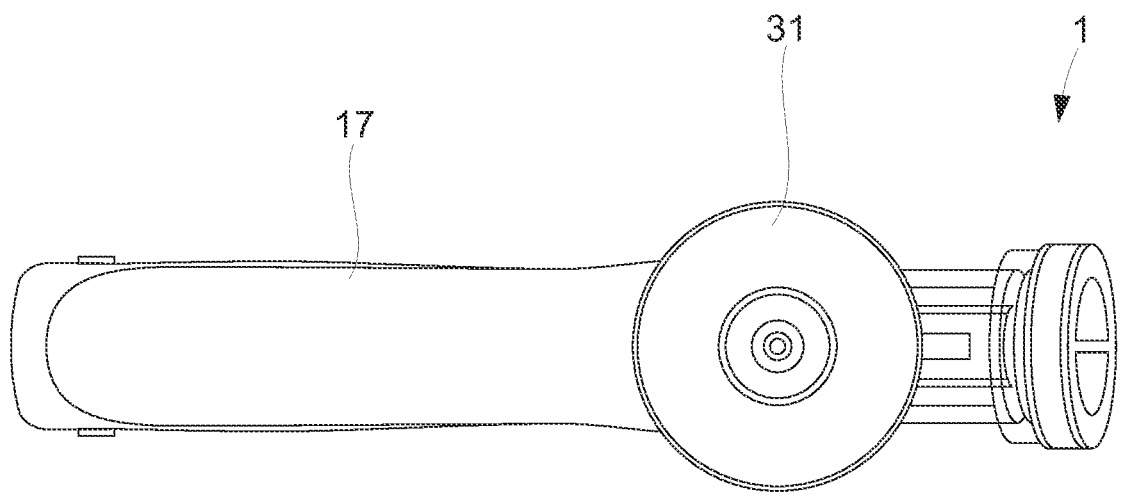
Figure 5:
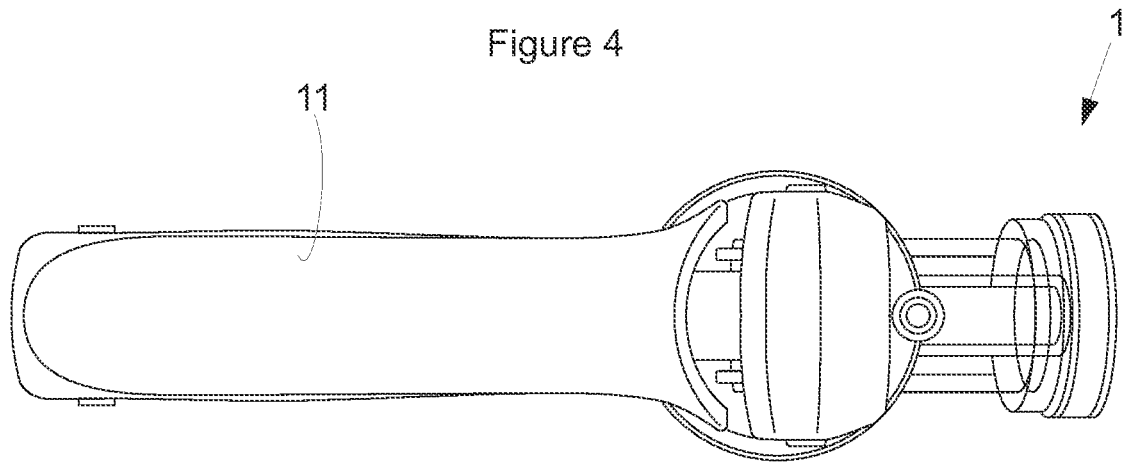
Figure 6:
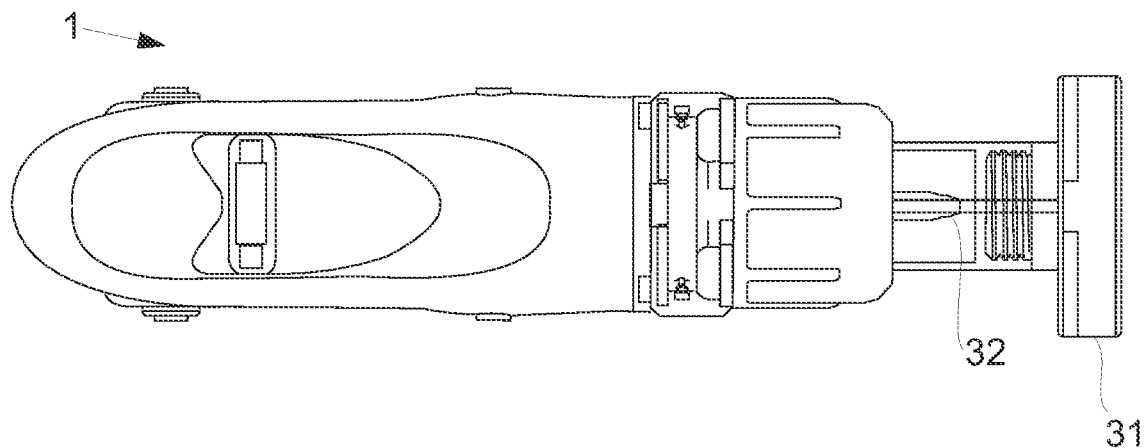
Figure 7:
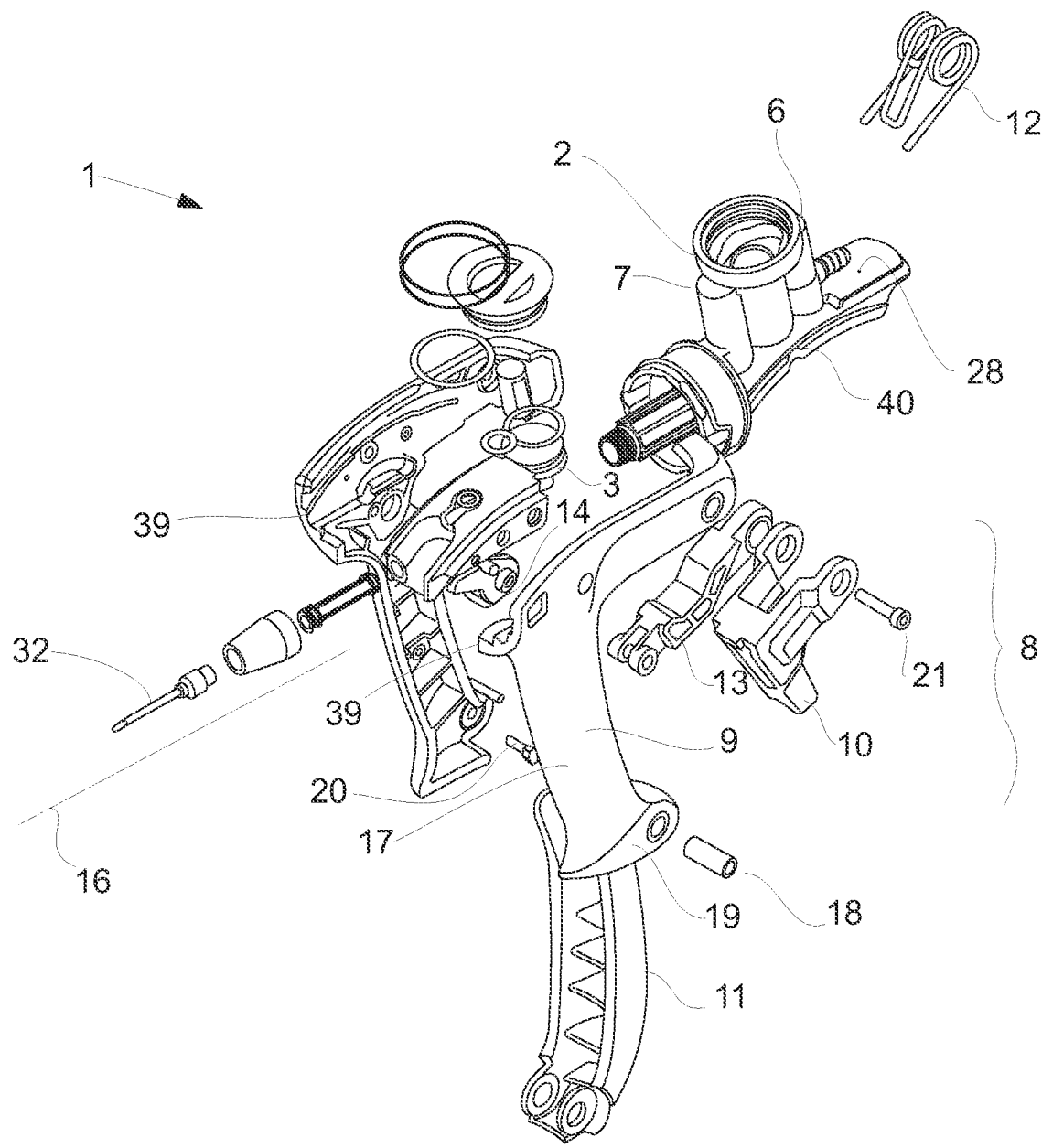
Figure 8:
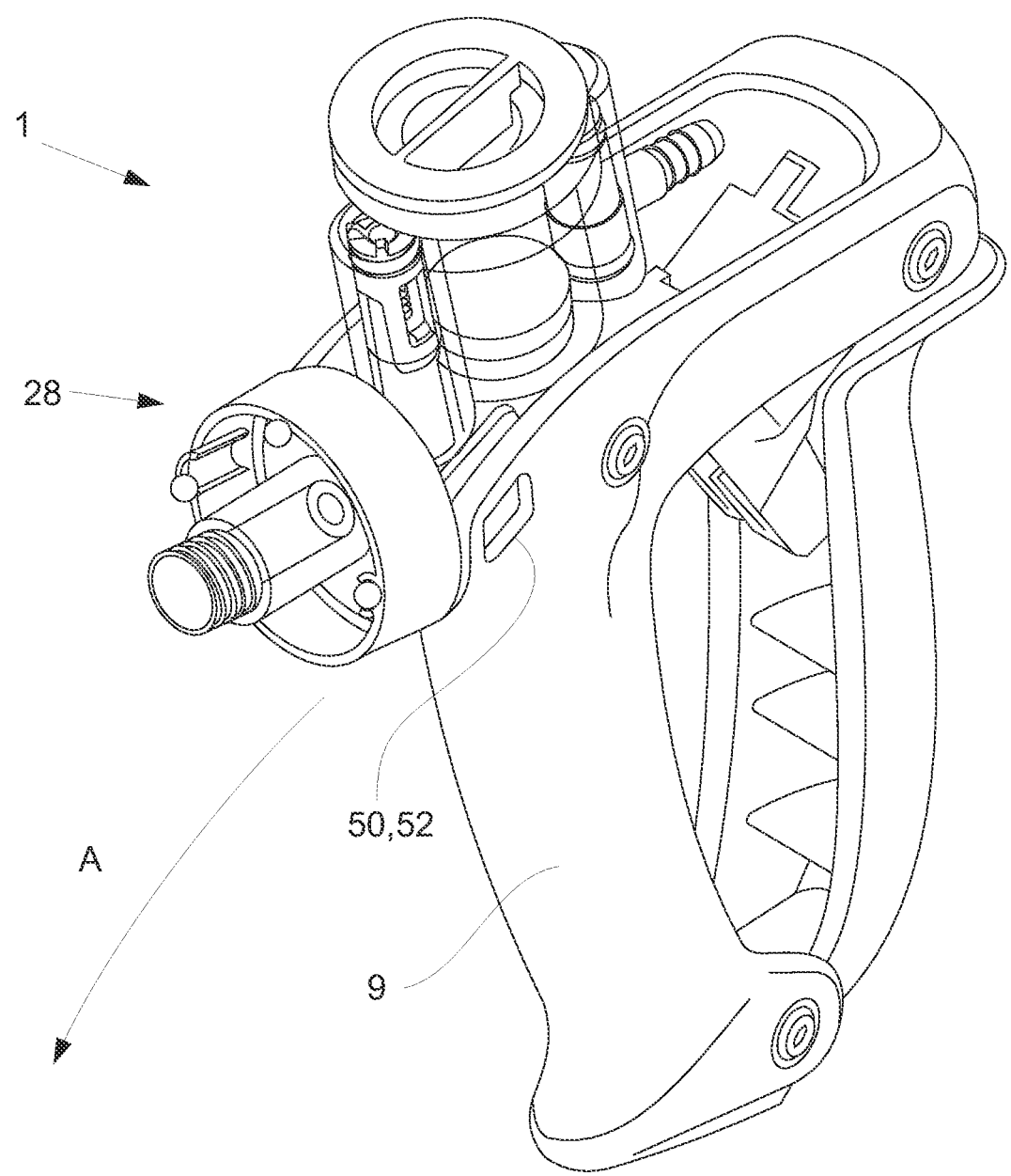

Preferred embodiments will now be described with reference to FIGS. 1 through 15.

The general layout of the applicator 1 is shown in FIGS. 1 through 8. The applicator 1 consists of a handle body 9 from which is mounted, and mainly housed the piston actuator assembly 8. Separably connected to the handle body 9 is the dose assembly 28. The dose assembly 28 is selectively removable from the handle body 9 resulting in two separable assemblies.

The applicator 1 has an applicator end 30 where the application is made to the animal. In the embodiment shown the applicator end has a marking pad 31 with an aperture there through for the application to be applied through. The application in this embodiment is via an injector 32 which is clearly visible, but is sheathed 37 and protected by the marking pad 31 and the trigger portion 22.

Present also is a locking portion 24, which in the embodiment shown takes the form of a locking barrel 25. Rotation of the locking barrel one way will enable the piston actuator assembly. Rotation in the other direction will disable the piston actuator assembly. In the embodiment shown the locking portion rotates and blocks the sliding motion of the sheath 37 which is transmitted to it by, in this case, contact of the marking pad 31 with the animal when applying a subcutaneous injection.

As shown the applicator 1 has a pistol grip for the user consisting of a handle component 17 which extends from and is connected to the handle body 9. At a distal end 19 of the handle component 17 is a first pivot point 18 from which is pivoted the user operated handle 11. It is this the user operates by squeezing to bring the two handle components 11 and 17 together to initiate the piston actuator assembly.

The dose assembly 28 consists of a fluid inlet 29 that connects to a supply of fluid, for example by flexible connection to a back pack, or to a directly mounted vial or similar.

The fluid inlet 29 leads to a one way inlet valve 6 which in turn leads to the barrel 3. Inside the barrel is a piston 3 that is slidingly sealed and can stroke from a first position 4 as shown to a second position 5, when allowed, to expel fluid in the barrel 2. The fluid is expelled as the piston 3 strokes to the second position 5 and exits the barrel 3 to the outlet valve 7 which then leads to fluid outlet 38 at or toward the applicator end 30. The fluid outlet 38 can have a number of differing effectors connected to it, in this case it has an injector 32, connecting in a known way using a hollow nut to hold it in place. The device end effector which applies the fluid to the animal could, instead of the injector 32, be configured in known ways to deliver the fluid, topically, nasally, orally or otherwise to the animal.

The fluid pathway of the fluid from fluid inlet, valving, barrel, piston, and fluid outlet is known method. However, what is different in the present invention is the change of orientation of the barrel. As shown the barrel 2, piston 3 and valves 6 and 7 are oriented so they do not lie along the main axis 16 of the injector. Typically doing so has led to many inefficiencies in design, and makes the applicator 1 longer. By effectively folding the fluid path and barrel, piston and valves out of this axis it allows for a more compact and maneuverable applicator 1.

The dose assembly 28 as described above from fluid inlet 29 to fluid outlet 38 is also a unitary assembly and holds the barrel 2, piston 3, valves 6 and 7, components used to vary the stop of the piston at the first or second position 5, such as inserts, or a variable stop.

Figure 10:
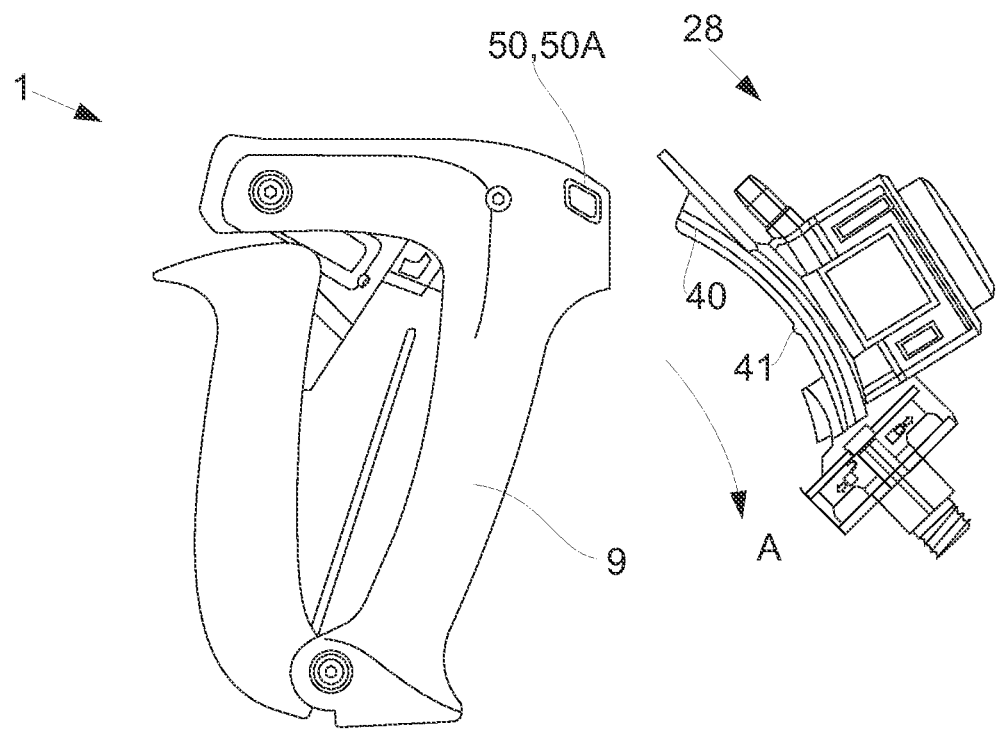
Figure 11:
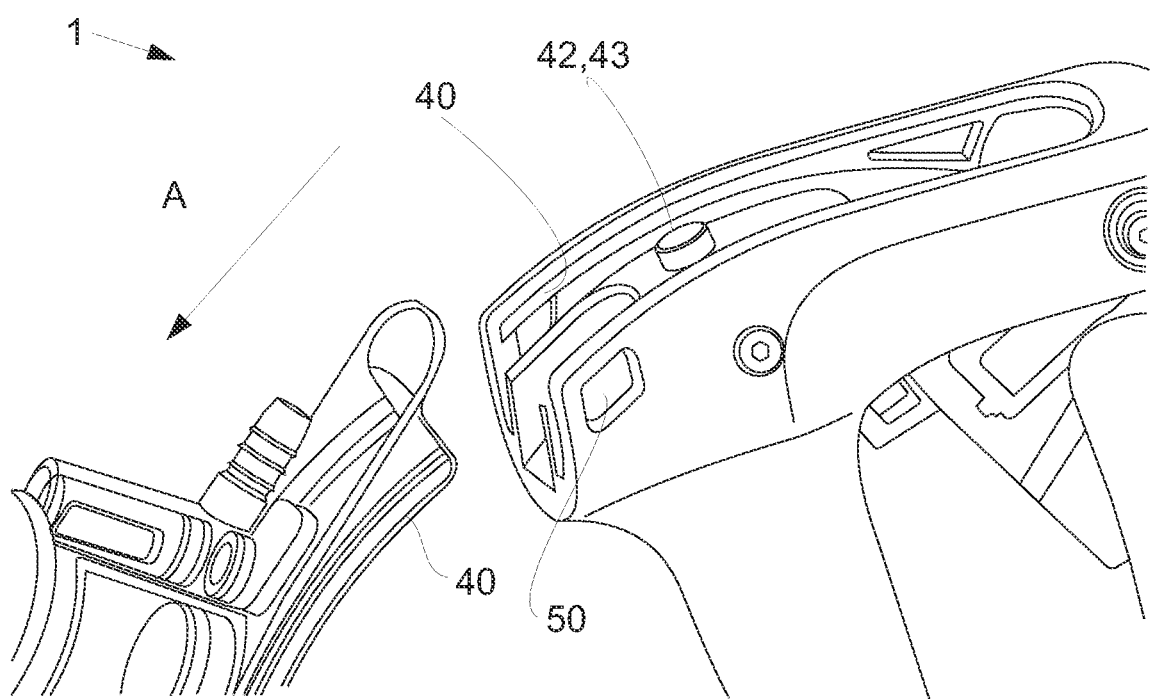

The dose assembly 28 is separable from the handle body 9 and engages via complimentary features in the handle body 9 and dose assembly 28 to interlock the two. In the embodiment shown the complimentary features are channels 39 in the handle body 9 as shown in FIG. 10, with complimentary rails 40 on the dose assembly 28. In the embodiment shown the rails 40 and channels 39 are curved. However, in other embodiments, they also could be straight, to also allow removal of the dose assembly 28 from the handle body 9.

Figure 9:
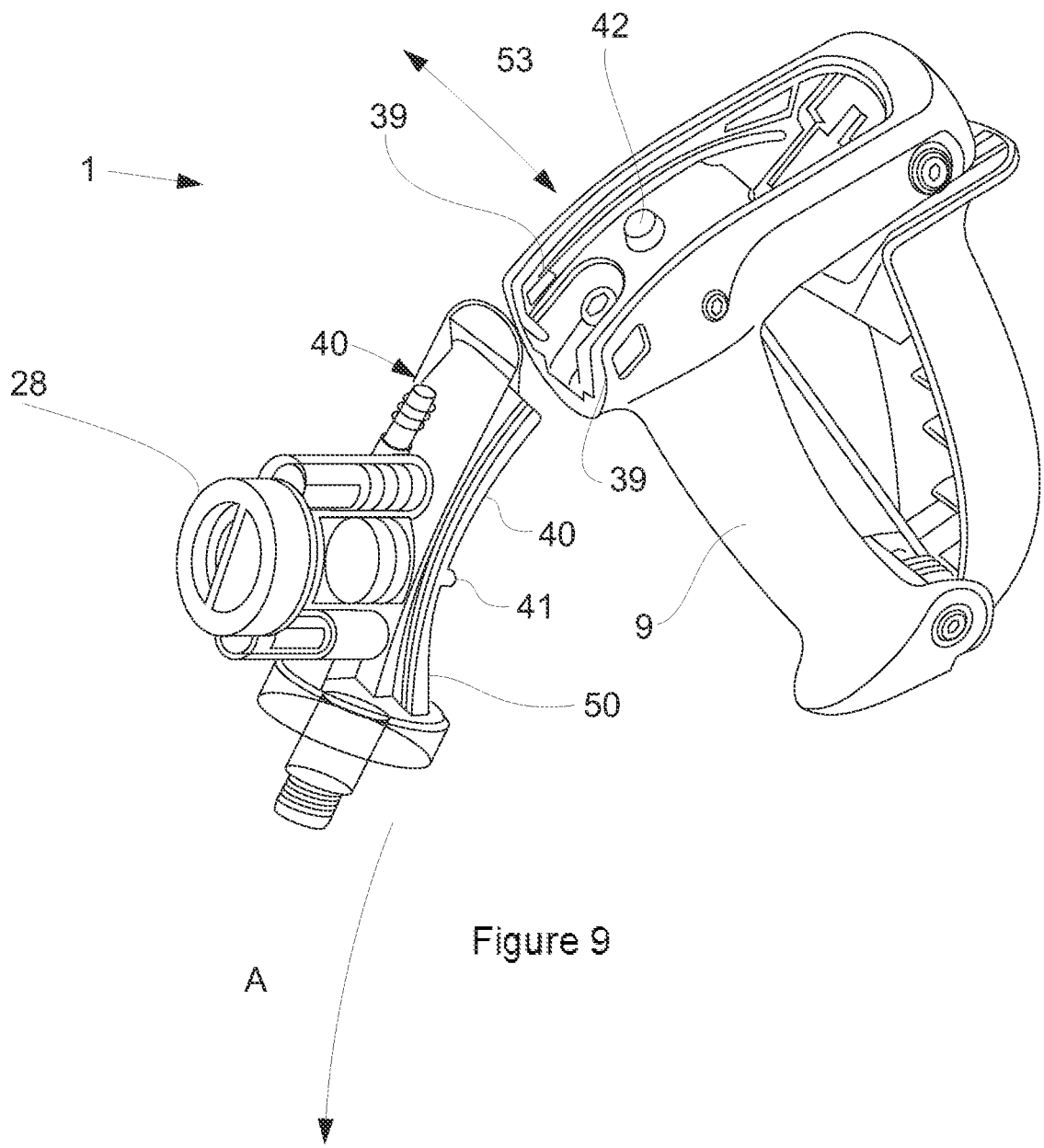

Removal of the dose assembly 28 from the handle body 9 is achieved by sliding the two relative to each other. In FIG. 9 sliding the dose body 28 in direction A relative to the handle body 9 allows separation of the two. Due to the curved nature of the rails 40 and channels 39 the direction A is also curved as also shown in FIG. 10.

The complimentary features of the dose body 28 and handle body 9 must resist the forces of general use of the applicator including the force applied by the handle body 9 to the dose assembly 28, in particular the piston 3. In the preferred configuration the piston 3 is driven generally upwards for dispensing fluid from the barrel 2, and downward for drawing fluid into the barrel. Upwards here is near to the vertical axis 51, that is within 0 to 25 degrees, and ideally as shown within 5 to 10 degrees off vertical axis 51 in FIG. 1. Therefore, the complimentary features between the dose assembly 28 and handle body 9 must resist these forces. Therefore, rails and channels as shown that are oriented at ninety degrees, or similar, to the sliding direction of movement of the piston from the first position 4 to the second position 5 is preferred. As shown the rails 40 and channels 39 are continuous and so release the dose assembly from the handle body in one continuous motion. However, in other embodiments the rails 40 and channels 39 may be intermittent such that only a small motion is required, much less than that shown in FIGS. 9 and 10, to disengage the rails 40 from the channels 39, and thereafter the dose assembly 28 can be lifted clear of the handle body 9. Such a broken or interrupted channel arrangement may be useful if only a small movement is desired to disengage the two.

It is desirable also to lock the dosing assembly 28 to the handle body 9 to prevent them being separated inadvertently, for example if they are knocked or similar. A further interlock 52 between the two is therefore present. In the embodiment shown this is by way of a cooperating detent 50, shown in FIGS. 9 and 10, between the dose assembly 28 and handle portion 9. In the embodiment shown the detent 50 takes the form of a window 50A in the handle portion 9, and a resilient protrusion 50B in the dose assembly. The two can move resiliently relative to each other in the lateral direction 53, that is perpendicular to the vertical axis 51 and perpendicular to the direction A. Likewise the protrusion 50B could be on the handle portion 9, or part thereof, connected directly or indirectly, and the window 50A could be on the dose assembly 28. In other embodiments there may be two protrusions that slide past each other to lock the two together. Present also may be a security pin that requires a controlled tool to unlock to prevent removal of the dose assembly 28 without authority.

The handle portion 9 as described actuates the piston 3 between the first 4 and second positions 5. The handle portion contains a piston actuator assembly 8 that deploys a piston actuator 42, which in turn bears on piston 3. In the preferred form there is a piston shaft 41 operably connected to the piston 3 to move it under action of the piston actuator 42. The piston shaft 41 is retained in the dose assembly 28 an the piston actuator 42 is retained in the handle body 9, this is shown for example in FIGS. 10-12. To enable removal of the dose assembly 28 from the handle portion 9 the connection between the piston actuator 42 must be a separable connection.

Figure 12:
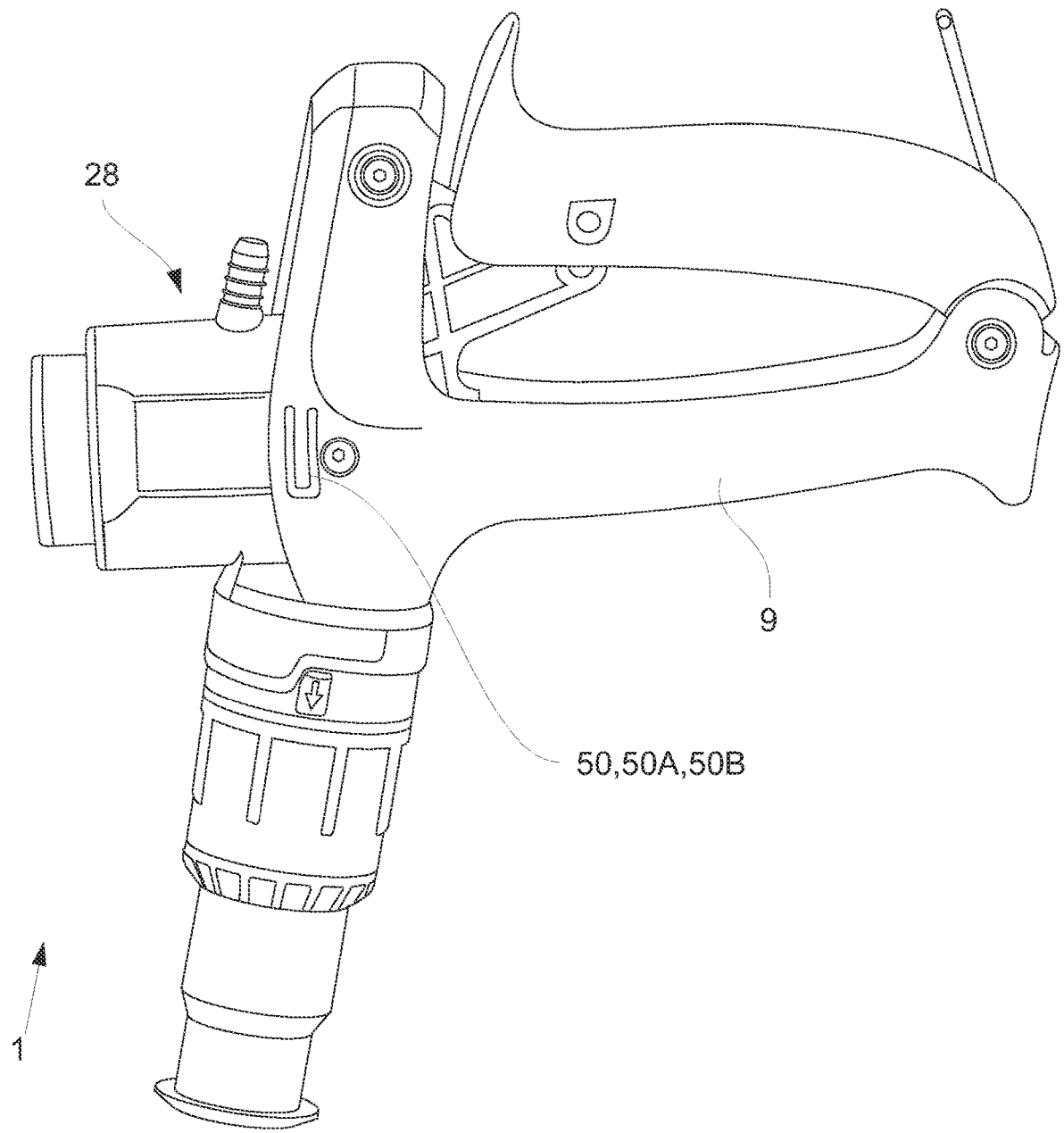
Figure 13:
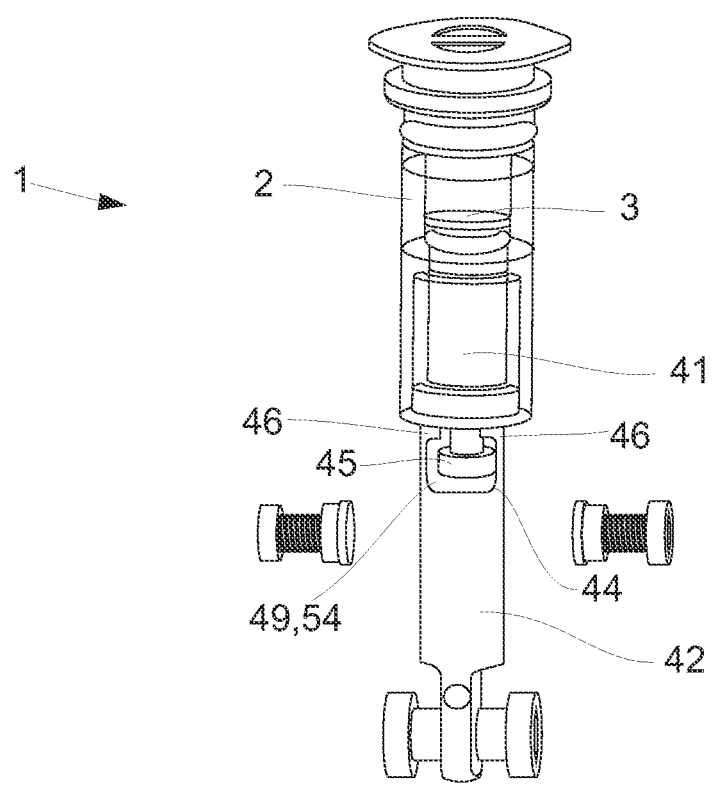

In one embodiment this separable connection is achieved by a magnetic connection between the two as shown for example in FIG. 12. A magnet may be on the piston actuator 42, to cooperate with another magnet or ferromagnetic material on the piston 3 and/or piston shaft 41, or vice versa. This separable connection will move the piston between the first and second position, but can be broken or separated when the dose assembly 28 is slid and removed from the handle portion.

Figure 14:
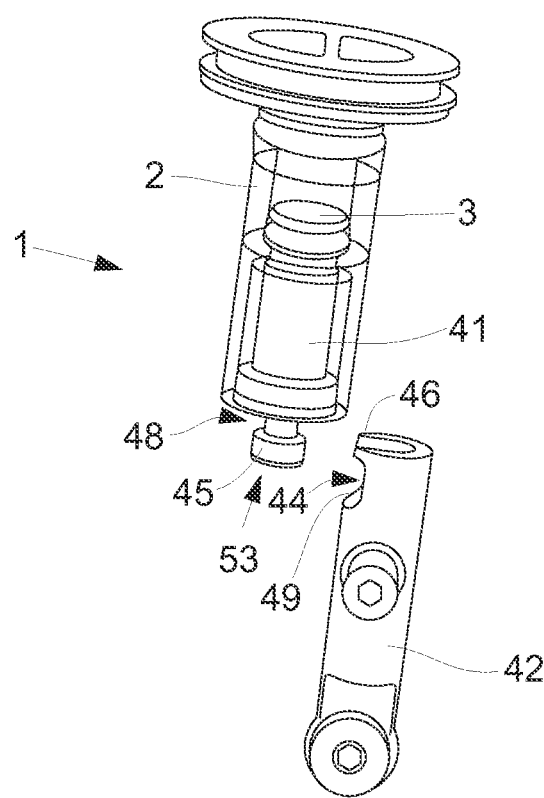

A similar embodiment for the separable connection is shown in FIGS. 14 and 15. In this embodiment the piston actuator 42 has a receptacle 44 to receive a bayonet 45 extending from the piston shaft 41, or vice versa. The receptacle 44 has one or more fingers 46 to engage over the shoulders 47 of the bayonet 45. The fingers 46 can pull the piston shaft 41 down to the first position, and push up, by hearing on the underside 48 of the piston shaft 41, or the pocket 49 of the receptacle 44 can bear on the low point 54 of the bayonet 45. In other forms the piston shaft 41 may have the receptacle 44 and the piston actuator 42 may have the bayonet 45.

In this way the piston actuator 42 can move the piston from the first position to the second position while connected to the piston, but then also be disconnected to allow removal of the dose assembly from the handle body 9.

In this way the dose assembly 28 and piston actuator assembly 8 as a handle assembly can be separated and joined. This allows quick change and servicing, but also where the barrel 2 is a fixed dose, allows changing of doses by changing the dose assembly 28 from a barrel 2 with one dose, to another dose assembly 28 with a barrel 2 of a differing dose.

This also allows rapid change of the functionality of the actuator 1, for example from a low dose injector, to a high dose topical actuator by simply exchanging one dose assembly 28 with another. All the while retaining the one handle body 9, thus cutting down on the cost of duplicating the handle body as well as the dose assembly.

The method of application and removal of the handle body 9 from the dose assembly 28 will now be described with reference to FIGS. 9 through 12. After the locking barrel is removed the dose assembly 28 can be slid from the handle assembly 8 as previously by disengaging the detents 50, or otherwise exceeding their locking capacity. Application of the dose assembly 28 to the handle body 9 is the reverse of this procedure.

In this way the dose assembly 28 can be separately removed from the piston actuating assembly 8, or handle assembly. This allows easy servicing, or replacement if damaged. Also in certain applications it may be desired to only have a dose assembly that has a single dose size, varying of the dose size requiring complete removal and replacement of the dose assembly 8 with another of a different size. Therefore, control of the dose assemblies can prevent incorrect dose sizes being applied.

The result is a more compact applicator 1 that also has the movement of the user operated handle 11 and handle component 17 having the ideal range of motion regardless of the dose that is delivered—from a small dose to a large dose the range of motion of the handles 11 and 17 is unchanged. The movement of the piston 3 is disconnected so that one does not affect the other from a range of motion perspective.

The foregoing description of the invention includes preferred forms thereof. Modifications may be made thereto without departing from the scope of the invention.

The invention claimed is:

1. An applicator, comprising:
a dosing body comprising:
at least one barrel;
a piston moveable within the at least one barrel to stroke between a first position and a second position, wherein, in use, movement of the piston towards the first position can draw a first fluid into the barrel, and movement of the piston towards the second position can force the first fluid out of the barrel;
at least one fluid inlet valve to allow the fluid to flow into the at least one barrel at least under action of the piston, and at least one fluid outlet valve to allow the first fluid to flow out of the at least one barrel at least under action of the piston; and
a piston actuating assembly deploying a piston actuator which in turn bears on the piston, the piston actuating assembly being selectively engageable with the dosing body via complimentary rails located on one side of the dosing body or the other, between the dosing body and the piston actuation assembly, the piston actuator assembly having a user operable handle to drive a second actuation member which in turn can drive the piston between the first position and the second position, a connection between the second actuation member being a releasable one;
the applicator having a longitudinal axis and an applicator end through which the fluid is ejected from the applicator, the fluid being ejected in a direction along the longitudinal axis of the applicator;
wherein the second actuation member and the piston actuator are arranged to move in a direction transverse to the longitudinal axis of the applicator.

2. The applicator according to claim 1 wherein the releasable connection is a magnetic one that attracts and holds, or a mechanical one that retains the second actuation member to the piston at least in the direction of movement of the piston.

3. The applicator according to claim 1 wherein there is a piston shaft between the piston and the second actuation member.

4. The applicator according to claim 1 wherein the piston and barrel are not in line with the second actuation member, but rather are at an angle to them, or a main axis of the applicator.

5. The applicator according to claim 1 wherein a handle component extends from the dosing body and the user operable handle pivots from a first pivot point at a distal end of the handle component.

6. The applicator according to claim 5 wherein the user operated handle is driven to extend away from the handle component by a second biasing component.

7. The applicator according to claim 1 wherein a first trigger component holds the second actuation member in place until a force is applied to release the first trigger component and the second actuation member.

8. The applicator according to claim 1 wherein the barrel is replaceable to vary the dose of the applicator.

9. The applicator according to claim 1 wherein the barrel can receive an insert to provide a stop of the second position of the piston to vary the dose of the applicator.

10. The applicator according to claim 1 wherein the barrel has a variable stop to vary the second position of the piston to vary the dose of the applicator.

11. The applicator according to claim 1 wherein the inlet valve, applicator, outlet valve, piston and barrel are removable as a dose assembly from the dosing body.

12. The applicator according to claim 1 wherein a second actuating component is held in position against the force of the first biasing component, a first trigger component holds the second actuating component in place until a required force is reached by the first biasing component, or a second trigger component releases the first trigger component, whereby the second actuating component is then released and driven by the force of the first biasing component to in turn drive the piston toward the second position.

13. The applicator as claimed in claim 1 therein the piston actuating assembly is at least in part contained within a handle portion, the handle portion engaging with the dose assembly.

14. A method of dispensing a fluid for animal welfare through an applicator, comprising the steps of:
a user driving a user operated handle which in turn drives a second actuating component of the applicator,
driving a piston via the second actuating component, where the second actuating component is housed in a unitary dose assembly including fluid inlet, inlet valve, barrel, outlet valve and fluid outlet,
the applicator including a piston actuating assembly deploying a piston actuator which in turn bears on the piston, the piston actuating assembly being selectively engageable with a dosing body containing the user operated handle via complimentary rails located on one side of the dosing body or the other, between the dosing body and the piston actuation assembly, operation of the piston from a first position to a second position driving a dose of fluid from the barrel to the fluid outlet for delivery,
the applicator having a longitudinal axis and an applicator end through which the fluid is ejected from the applicator in a direction along the longitudinal axis of the applicator;
wherein the second actuation member and the piston actuator are arranged to move in a direction transverse to the longitudinal axis of the applicator.

* * * * *